(12) United States Patent
Meirav et al.

(10) Patent No.: US 7,560,702 B2
(45) Date of Patent: Jul. 14, 2009

(54) INTERCONNECT AND PACKAGING METHOD FOR MULTI-SLICE CT DETECTOR MODULES

(75) Inventors: Oded Meirav, Haifa (IL); David Michael Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 264 days.

(21) Appl. No.: 11/287,655

(22) Filed: Nov. 28, 2005

(65) Prior Publication Data

US 2007/0121781 A1    May 31, 2007

(51) Int. Cl.
    *H01L 27/146* (2006.01)
(52) U.S. Cl. .............................. 250/370.13; 250/370.09
(58) Field of Classification Search ............ 250/370.13, 250/370.09
    See application file for complete search history.

(56) References Cited

U.S. PATENT DOCUMENTS

| | | | | |
|---|---|---|---|---|
| 5,245,191 A | * | 9/1993 | Barber et al. | .......... 250/363.04 |
| 5,644,102 A | * | 7/1997 | Rostoker | .................... 174/547 |
| 6,139,337 A | * | 10/2000 | Englert et al. | ................. 439/91 |
| 6,510,195 B1 | * | 1/2003 | Chappo et al. | ................ 378/19 |
| 6,807,248 B2 | | 10/2004 | Mihara et al. | ................. 378/10 |
| 2004/0065465 A1 | * | 4/2004 | Chappo et al. | ................ 174/66 |
| 2004/0120448 A1 | * | 6/2004 | Ratzmann | ....................... 378/4 |
| 2005/0094763 A1 | * | 5/2005 | Sherman et al. | ............... 378/19 |

* cited by examiner

*Primary Examiner*—David P Porta
*Assistant Examiner*—Shun Lee
(74) *Attorney, Agent, or Firm*—Cantor Colburn LLP

(57) ABSTRACT

Disclosed herein is a computed tomography (CT) detector module, for coupling with a collimator rail. The CT detector module includes a CT detector pack, a printed circuit board, and electrical conductor, and a substrate. The electrical conductor is disposed between and in electrical communication with the CT detector pack and the printed circuit board. The substrate has a slot and is disposed between the CT detector pack and the circuit board such that the electrical conductor is routed through the slot.

19 Claims, 9 Drawing Sheets

INTERCONNECT AND PACKAGING METHOD FOR MULTI-SLICE CT DETECTOR MODULES

BACKGROUND OF THE INVENTION

This application relates generally to Computed Tomography (CT) systems. In particular, the invention relates to an interconnect and packaging method for multi-slice CT detector modules. CT systems are used to obtain non-invasive sectional images of test objects, particularly internal images of human tissue for medical analysis and treatment. In a computed tomography (CT) system, an x-ray source projects a fan-shaped beam that is collimated to lie within an X-Y plane of a Cartesian coordinate system, termed the "imaging plane." The x-ray beam passes through the object being imaged, such as a medical patient, and impinges upon a multi-row multi-column detector array. The detector array comprises a plurality of detector elements. The detector system converts incident X-rays of varying intensity into electronic signals. CT system detector electronics use integrated circuit boards that process electronic the signals during CT system scans.

Two types of radiation detectors are used in CT systems: scintillation detectors and direct conversion detectors. New pixilated direct-conversion (DC) CT detector modules require stringent packaging, interconnect and mounting solutions to be properly installed on a CT scanner collimator-grid assembly.

Compatibility between both types of radiation detectors is desirable so that the new DC modules may be mounted directly onto a nominal collimator while meeting all required common design specifications (for example, independent module mount/remount capabilities, high-precision alignment to the collimator assembly using existing dual alignment pin, "pin-in-pack" methods, thermal heat transfer performance, and mechanical robustness).

The ability to upgrade the CT detector modules and components must also be provided, in particular, a configuration is needed that supports both 20 mm/32 slice and 40 mm/64 slice detector-pack 2D tilability.

BRIEF SUMMARY OF THE INVENTION

Disclosed herein is a computed tomography (CT) detector module, for coupling with a collimator rail. The CT detector module includes a CT detector pack, a printed circuit board, and electrical conductor, and a substrate. The electrical conductor is disposed between and is in electrical communication with the CT detector pack and the printed circuit board. The substrate has a slot and is disposed between the CT detector pack and the circuit board such that the electrical conductor is routed through the slot.

Further disclosed herein is a computed tomography (CT) detector array. The CT detector array includes a first and a second collimator rail, a plurality of CT detector modules, and an elastomer conducting contact. The second collimator rail has a high voltage strip and is spaced adjacent to the first collimator rail. Each of the CT detector modules has a CT detector pack, a printed circuit board, an electrical conductor, and a substrate. The electrical conductor is disposed between and is in electrical communication with the CT detector pack and the printed circuit board. The substrate has a slot and is disposed between the CT detector pack and the circuit board such that the electrical conductor is routed through the slot and the substrate is mounted on the first collimator rail and the second collimator rail. The elastomer conducting contact is disposed within the substrate and is in electrical communication with the CT pack such that the elastomer conducting contact and the high voltage strip are electrically connected.

Yet further disclosed herein is a method for electrically connecting a computed tomography (CT) module to a CT system. A CT detector pack is attached to a substrate having a slot. An electrical conductor is routed from the CT detector pack, through the substrate slot, and to a printed circuit board. The substrate is mounted to a plurality of collimator rails such that an electrical connection is formed when the substrate is mounted to the collimator rails.

BRIEF DESCRIPTION OF THE DRAWINGS

Referring to the exemplary drawings wherein like elements are numbered alike in the accompanying Figures.

DETAILED DESCRIPTION OF THE INVENTION

Figure 1:
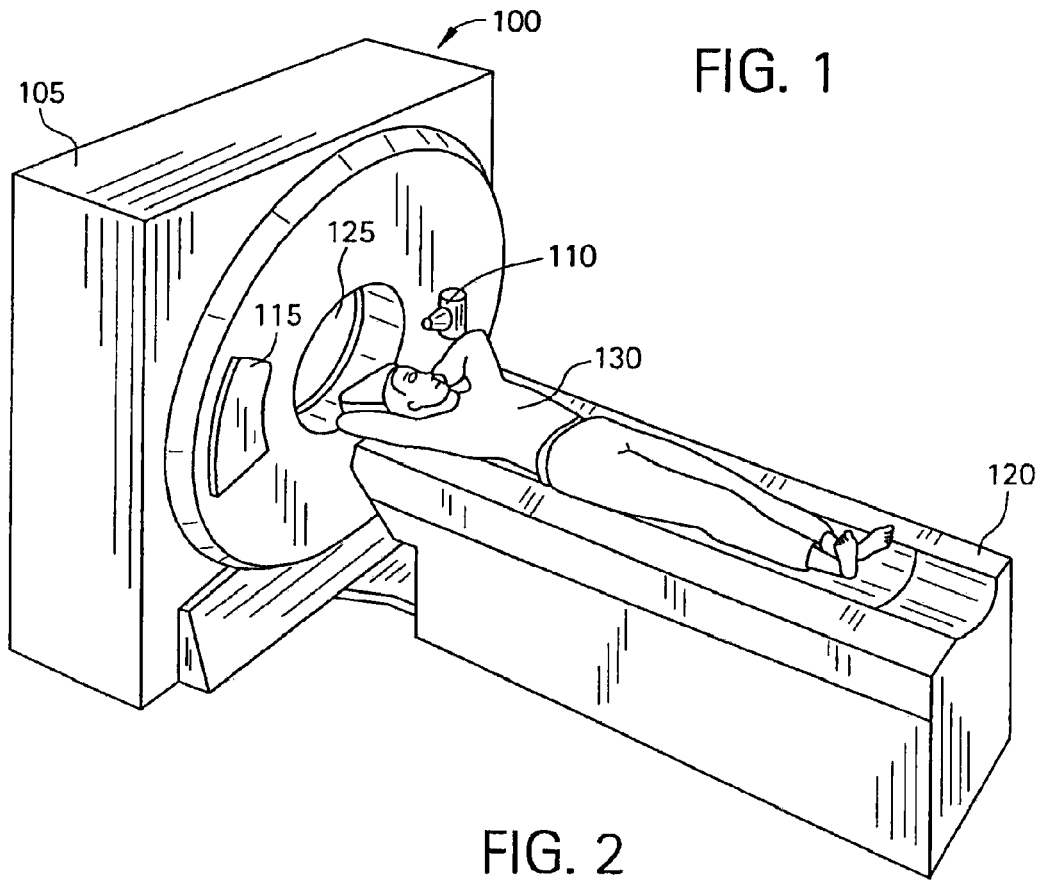
FIG. 1 is a perspective view of a CT imaging system and a patient disposed for imaging in accordance with an exemplary embodiment.
Figure 2:
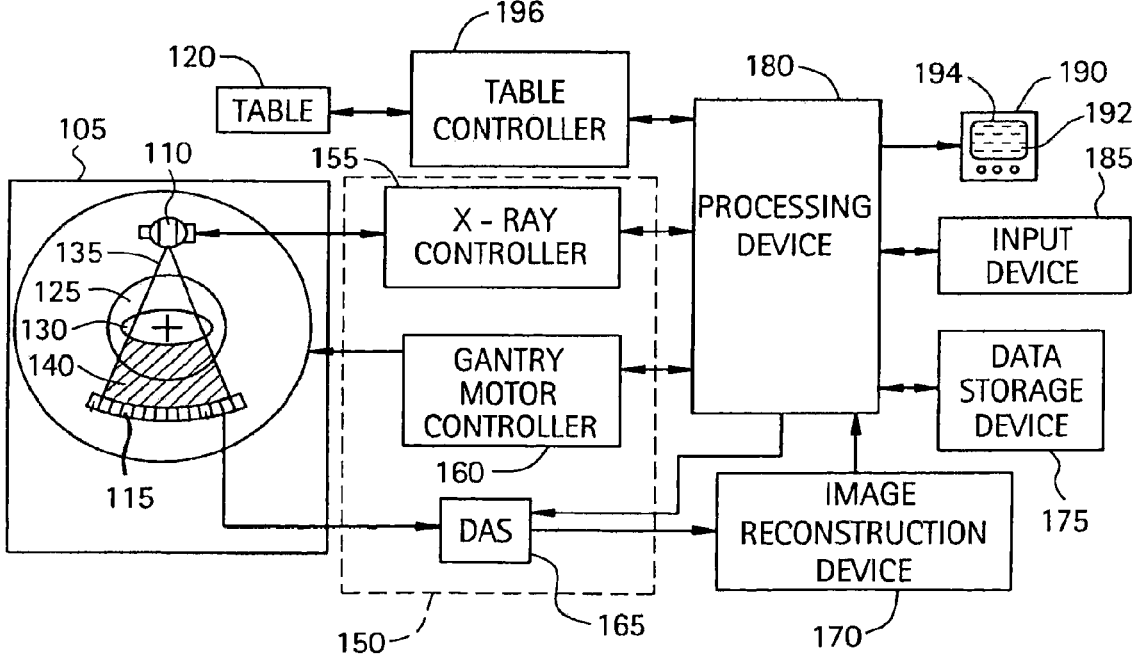
FIG. 2 is a block schematic diagram of the CT imaging system of FIG. 1 for use in accordance with an exemplary embodiment.

FIGS. 1 and 2 illustrate an exemplary CT imaging system 100 including a gantry 105 having an x-ray source 110, a radiation detector array 115, a patient support structure 120 and a patient cavity 125, wherein the x-ray source 110 and the radiation detector array 115 are opposingly disposed so as to be separated by the patient cavity 125. In an exemplary embodiment, a patient 130 is disposed upon the patient support structure 120, which is then disposed within the patient cavity 125. The x-ray source 110 projects an x-ray beam 135 toward the radiation detector array 115 so as to pass through the patient 130. In an exemplary embodiment, the x-ray beam 135 is collimated by a collimate (not shown) so as to lie within an X-Y plane of a Cartesian coordinate system referred to as an "imaging plane". After passing through and becoming attenuated by the patient 130, the attenuated x-ray beam 140 is received by the radiation detector array 115. The radiation detector array 115 receives an attenuated x-ray beam 140 and produces an electrical signal responsive to the intensity of the attenuated x-ray beam 140.

In addition, the x-ray source 110 and the radiation detector array 115 are rotatingly disposed relative to the gantry 105 and the patient support structure 120, so as to allow the x-ray source 110 and the radiation detector array 115 to rotate around the patient support structure 120 when the patient support structure 120 is disposed within the patient cavity 125. X-ray projection data is obtained by rotating the x-ray source 110 and the radiation detector array 115 around the patient 130 during a scan. The x-ray source 110 and the radiation detector array 115 communicate with a control mechanism 150 associated with the CT imaging system 100. The control mechanism 150 controls the rotation and operation of the x-ray source 110 and the radiation detector array 115.

In an exemplary embodiment, the control mechanism 150 includes an x-ray controller 155 communicating with an x-ray source 110, a gantry motor controller 160, and a data acquisition system (DAS) 165 communicating with a radiation detector array 115. The x-ray controller 155 provides power and timing signals to the x-ray source 110, the gantry motor controller 160 controls the rotational speed and angular position of the x-ray source 110, and the radiation detector array 115 and the DAS 165 receive the electrical signal data for subsequent processing. In an exemplary embodiment, the CT imaging system 100 also includes an image reconstruction device 170, a data storage device 175 and a processing device 180, wherein the processing device 180 communicates with the image reconstruction device 170, the gantry motor controller 160, the x-ray controller 155, the data storage device 175, an input device 185 and an output device 190. The CT imaging system 100 can also include a table controller 196 in communication with the processing device 180 and the patient support structure 120, so as to control the position of the patient support structure 120 relative to the patient cavity 125.

In accordance with an exemplary embodiment, the patient 130 is disposed on the patient support structure 120, which is then positioned by an operator via the processing device 180 so as to be disposed within the patient cavity 125. The gantry motor controller 160 is operated via processing device 180 so as to cause the x-ray source 110 and the radiation detector array 115 to rotate relative to the patient 130. The x-ray controller 155 is operated via the processing device 180 so as to cause the x-ray source 110 to emit and project a collimated x-ray beam 135 toward the radiation detector array 115 and hence toward the patient 130. The x-ray beam 135 passes through the patient 130 so as to create an attenuated x-ray beam 140, which is received by the radiation detector array 115.

The radiation detector array 115 receives the attenuated x-ray beam 140, produces electrical signal data responsive to the intensity of the attenuated x-ray beam 140 and communicates this electrical signal data to the DAS 165. The DAS 165 then converts this electrical signal data to digital signals and communicates both the digital signals and the electrical signal data to the image reconstruction device 170, which performs high-speed image reconstruction. This information is then communicated to the processing device 180, which stores the image in the data storage device 175 and displays the digital signal as an image via output device 190. In accordance with an exemplary embodiment, the output device 190 includes a display screen 194 having a plurality of discrete pixel elements 192.

Figure 3:
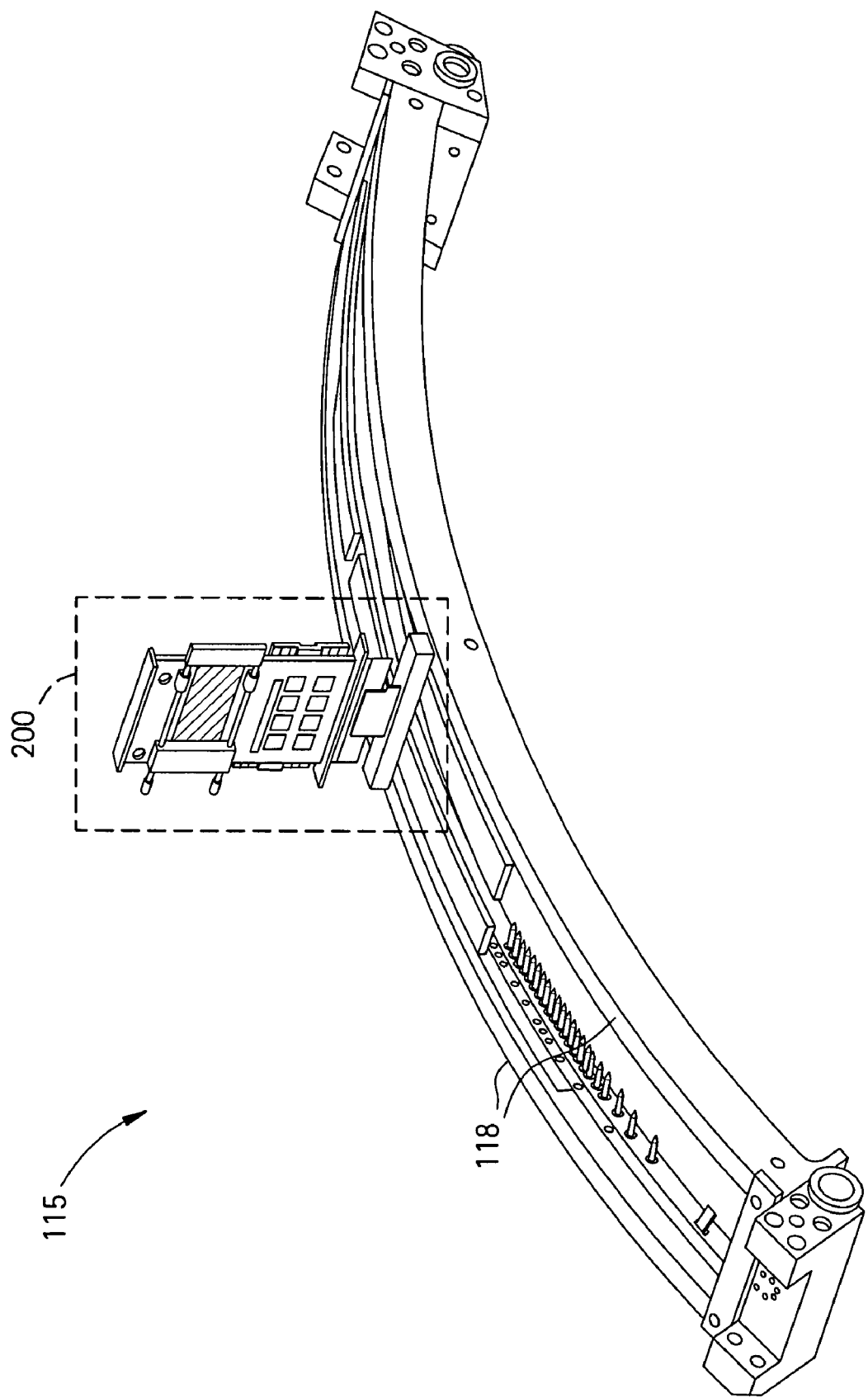
FIG. 3 is a perspective view of an exemplary radiation detector array for use in accordance with an embodiment of the invention.

FIG. 3 further illustrates an exemplary radiation detector array 115, also referred to as a CT detector array, having collimator rails 118 and a CT detector module 200. The radiation detector array 115 includes a plurality of CT detector modules 200 disposed along an outer periphery of the collimator rails 118, although only one CT detector module 200 is depicted in FIG. 3 for clarity of illustration.

Exemplary embodiments of the CT detector module 200 include several features to allow for close compatibility between new pixilated direct conversion (DC) CT detector modules, for example cadmium telluride (CdTe) modules or cadmium zinc telluride (CZT) modules, which may be fabricated by, for example, a company such as DxRay, Inc., and scintillation CT detector modules, such as for example volume CT (VCT) Lumex™ modules available from General Electric Company. These features enable the sharing of many existing VCT data acquisition system (DAS) solutions and technologies leading to significant cost savings for future CdTe-based and CZT-based VCT scanners.

Figure 4:
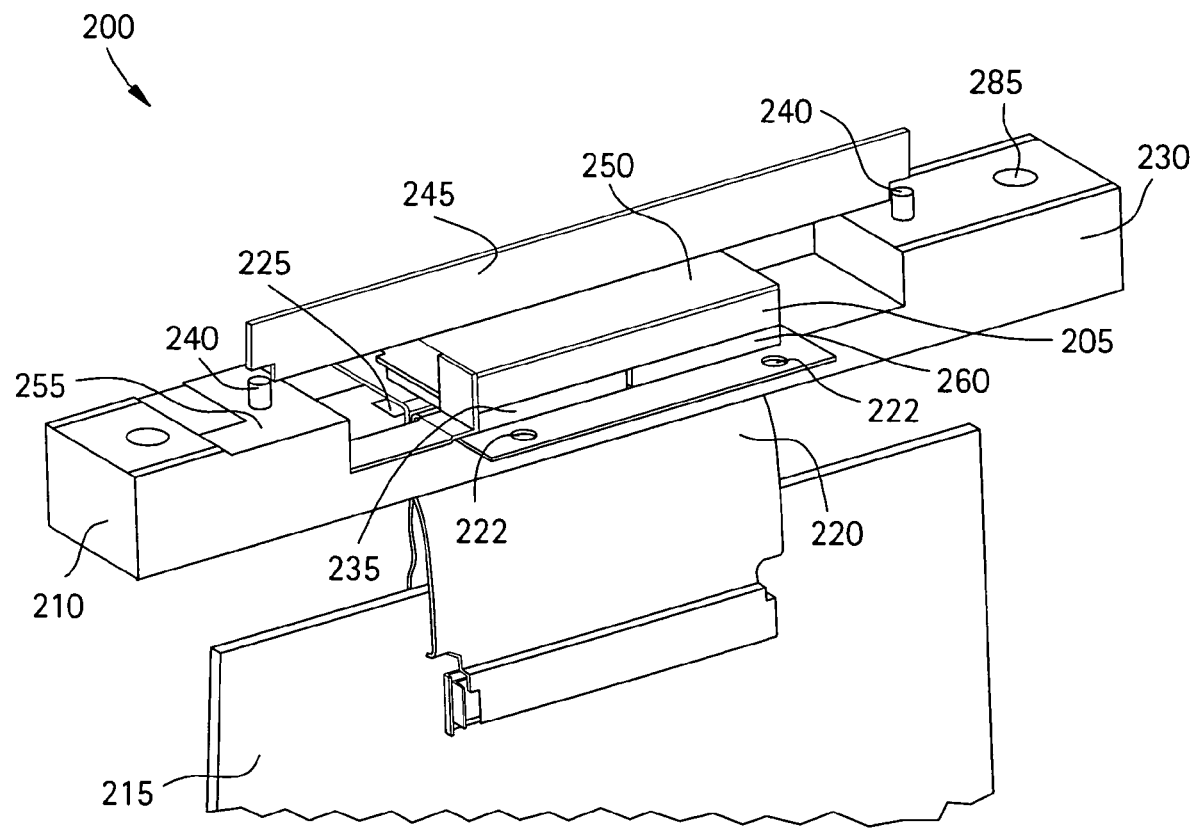
FIG. 4 is a perspective view of an exemplary CT detector module and printed circuit board for use in accordance with an embodiment of the invention.

FIG. 4 further illustrates an exemplary embodiment of the CT detector module 200. The CT detector module 200 includes a substrate 210, which may be ceramic or metallic, having a feed through slot 225, anti-scatter collimator plates 245, alignment pins 240 and mounting pads 230 for proper mating to the collimator rails 118, and a CT detector pack 205, such as a CdTe pack or a CZT pack for example, disposed between an insulative and conductive cathode 250 and a pitch adapter 260 and ball grid array (BGA) 235.

Figure 5:
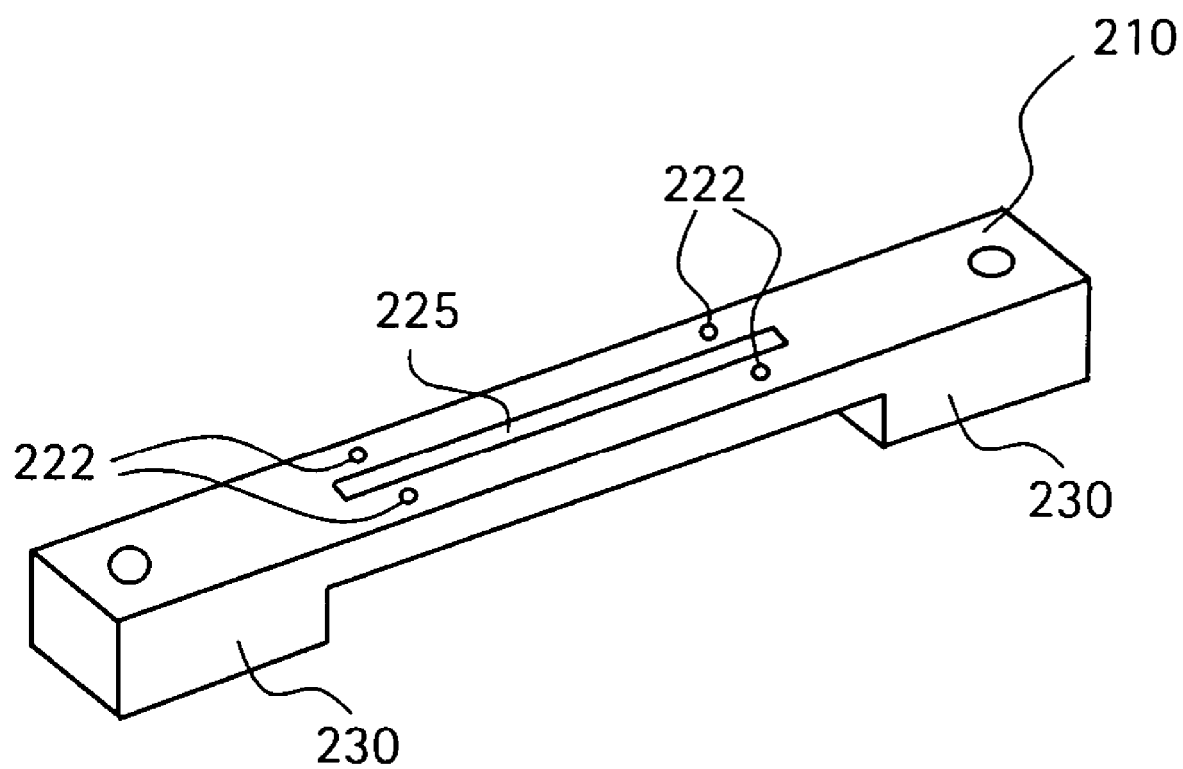
FIG. 5 is a perspective view of an exemplary substrate for use in accordance with an embodiment of the invention.

The feed through slot 225 (better illustrated in FIG. 5) allows for a plurality of flexible conductors 220, such as flex cables for example, to pass through the substrate and provide an electrical connection between the BGA 235 and a printed circuit board (PCB) 215.

Figure 6:
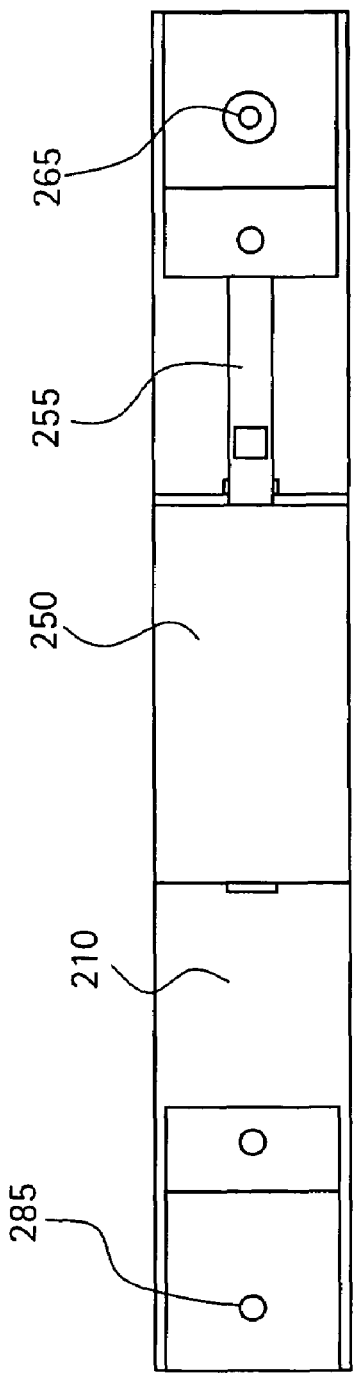
FIG. 6 is a top view of an exemplary CT detector module for use in accordance with the invention.
Figure 7:
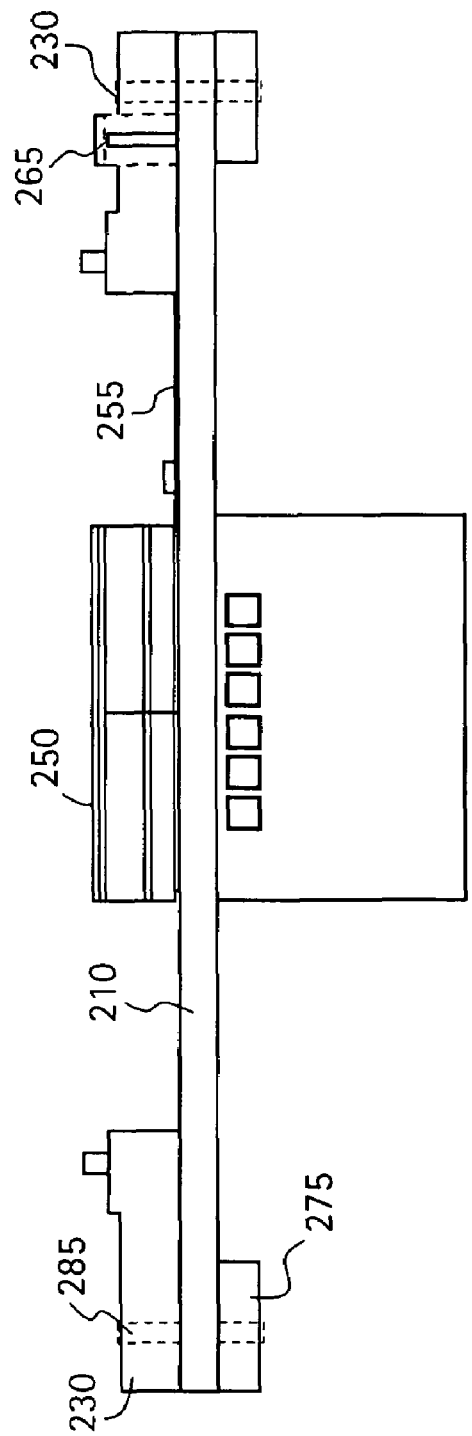
FIG. 7 is a side view of an exemplary CT detector module for use in accordance with an embodiment of the invention.
Figure 8:
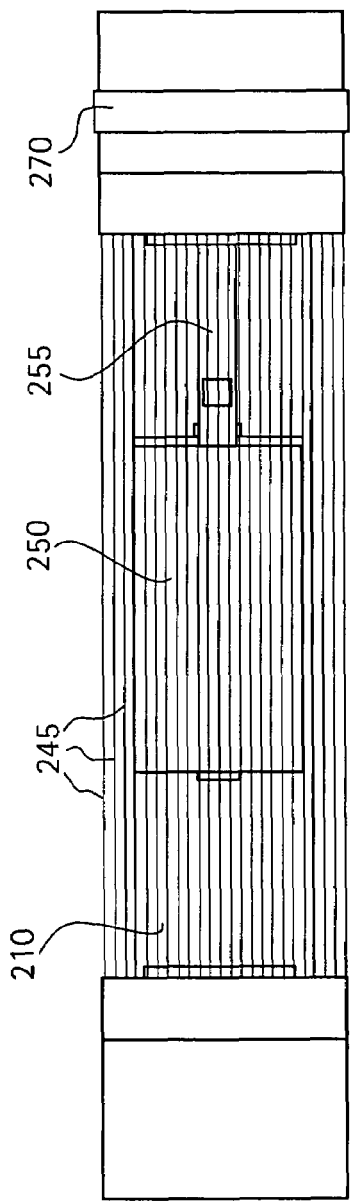
FIG. 8 is a top view of an exemplary CT detector module mounted on collimator rails for use in accordance with an embodiment of the invention.
Figure 9:
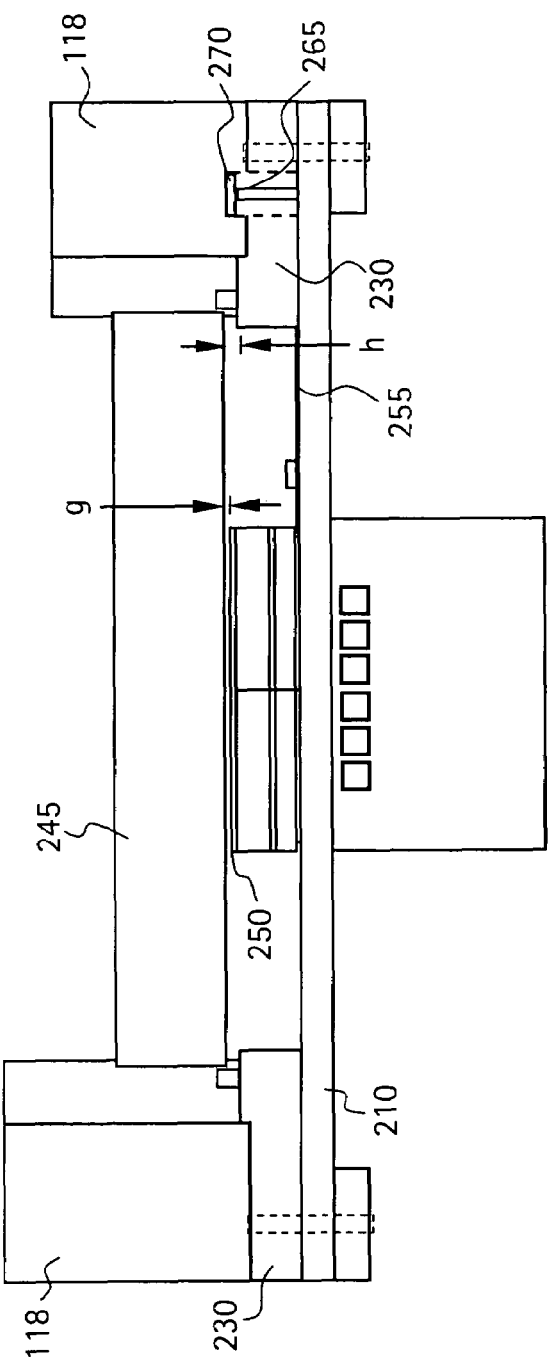
FIG. 9 is a side view of an exemplary CT detector module mounted on collimator rails for use in accordance with an embodiment of the invention.

The mounting pads 230 and alignment pins 240, which may be attached or integral to an end of the substrate 210, are further illustrated in FIGS. 6-9. FIGS. 6 and 7 depict the CT detector module 200 before installation while FIGS. 8 and 9 depict the CT detector module 200 installed on the collimator rails 118. The pad 230 height, shown as dimension "h" in FIG. 9, assures proper separation, shown as gap "g" in FIG. 9, of the detector cathode 250 from the collimator plates 245. The mounting pads 230 further include a hole 285 which is precisely machined into each of the pads 230 which together with the alignment pins 240 provide a dual alignment feature and proper mating to the collimator rails 118 and CT system 100. Module attachment to the collimator rails 118 remains as a common interface, wherein bolts are inserted through the collimator rails 118, passing through the mounting pads 230 and the substrate 210, secured into a threaded block 275, which is disposed below the substrate, thus allowing for interchangeability between DC detector modules and scintillation modules.

The CT detector module 200 further includes a high voltage (HV) strip 270, as depicted in FIGS. 8 and 9. A common high voltage strip 270 with suitable spaced contact points is fastened to one of the collimator rails 118. On each detector module 200 an elastomer 265 with a central conducting contact is fitted into the mounting pad 230. On each detector module 200 a HV line 255 is used to connect between the CdTe or CZT cathode 250 and the elastomer conducting contact 265. The presented arrangement of the HV elastomer 265 and the HV line 255 allows for a high voltage anode signal to be provided to each detector module 200 when it is fitted and pressed (forming a press fit electrical connection) on to the collimator rail 118.

A signal connection feature is further embodied wherein two opposing flexible conductors 220, as shown in FIG. 4, are fastened to the substrate 210 at points 222. BGA 235 contacts on different types of detector packs (for example CdTe, CZT, or VCT Lumex™) are precisely positioned relative to the alignment pins 240 and fastened to the flexible conductors 220 which are connected to transfer electrical signals to the printed circuit board 215.

Figure 10:
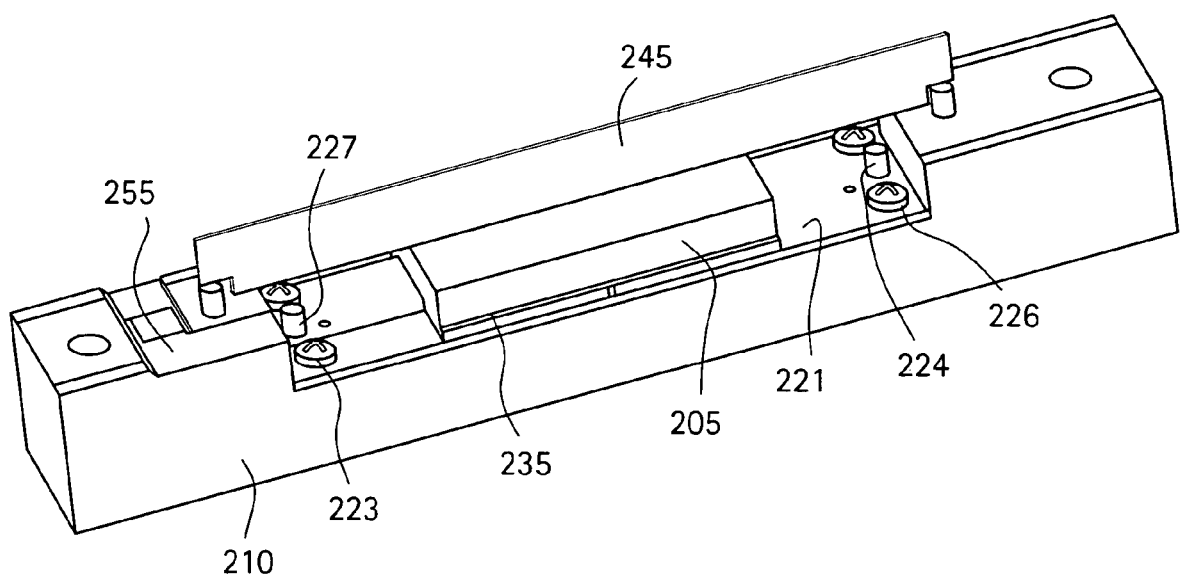
FIG. 10 is a perspective view of an exemplary CT detector module for use in accordance with an embodiment of the invention.
Figure 11:
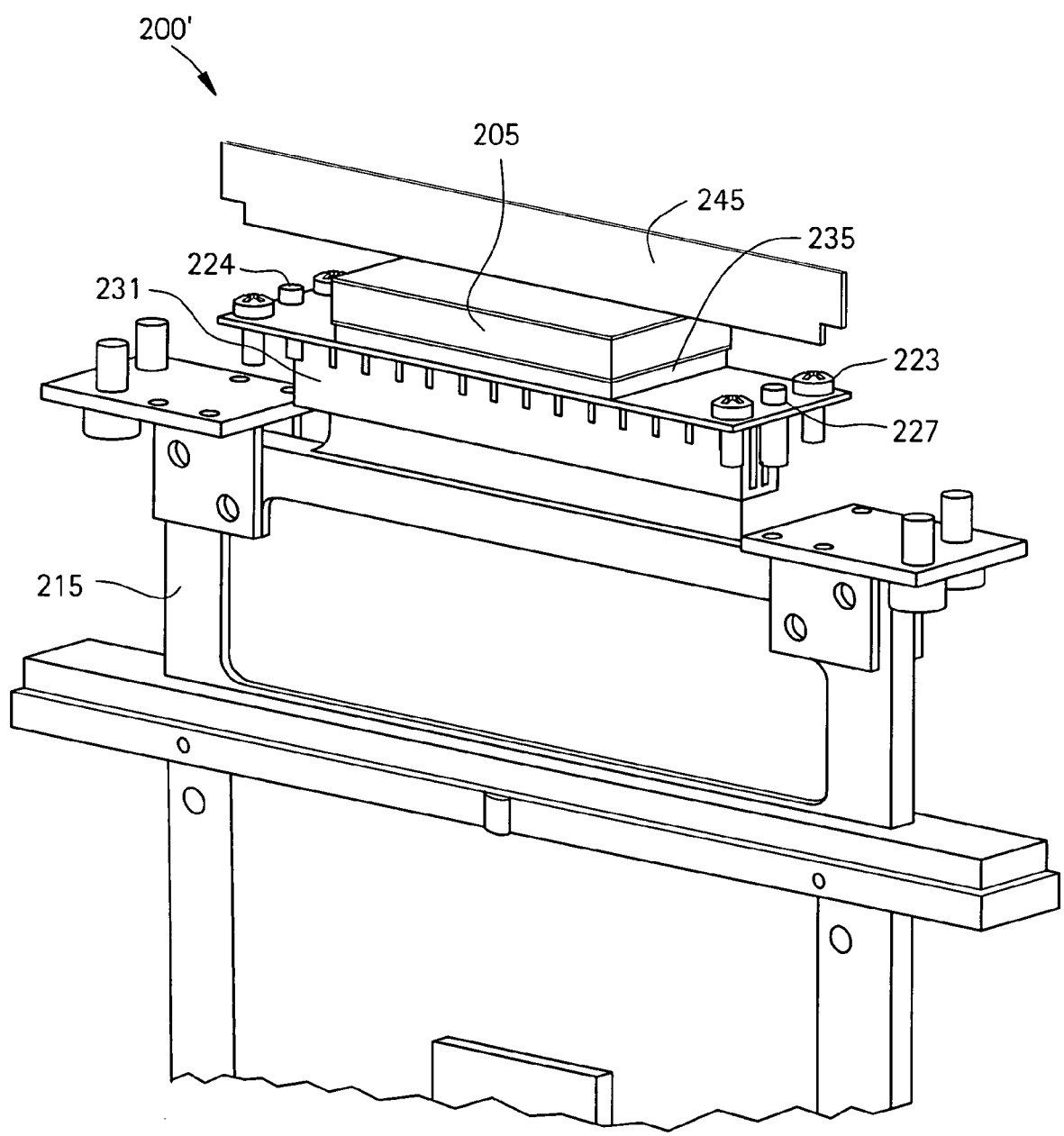
FIG. 11 is a perspective view of an exemplary CT detector module and printed circuit board for use in accordance with an embodiment of the invention.
Figure 12:
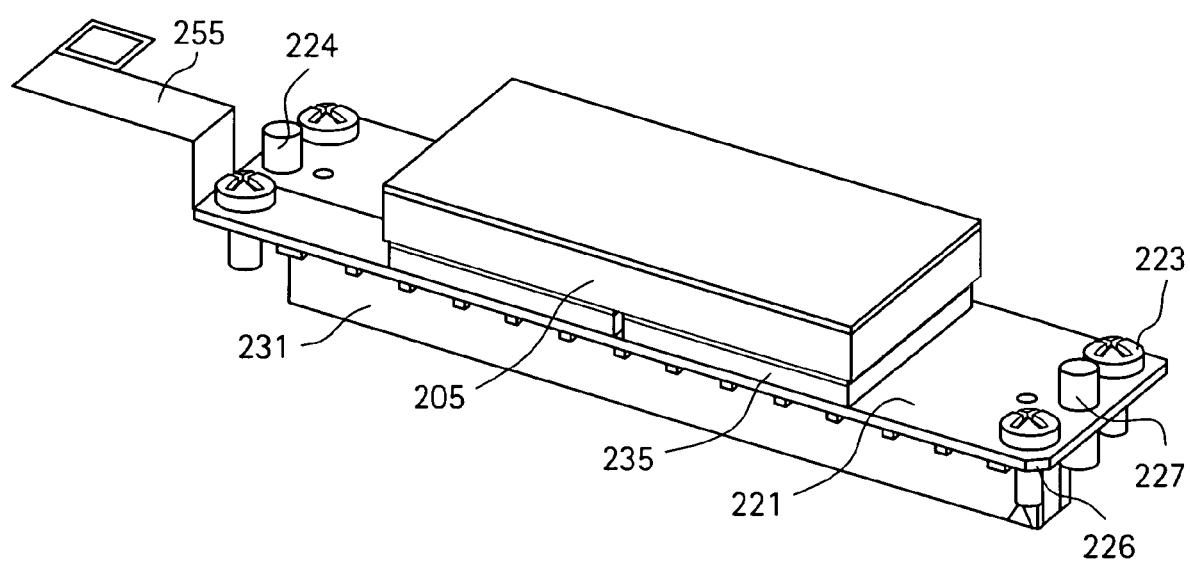
FIG. 12 is a partial view of an exemplary CT detector module for use in accordance with an embodiment of the invention.

FIG. 10 illustrates an alternative embodiment of a CT detector module 200' (printed circuit board 215 not shown for clarity) wherein the flexible conductors 220 are replaced by a printed circuit board, hereinafter referred to as an Interface Adapting Board (IAB) 221, and an electrical connector 231 (illustrated in FIGS. 11 and 12), which may be an 120-pin 0.8 mm pitch connector for example. The Interface Adapting Board 221 and the electrical connector 231 provide for an electrical connection, through the feed through slot 225, between the BGA 235 and the printed circuit board 215 as illustrated in FIG. 10 (substrate 210 not shown). The Interface Adapting Board 221 is secured to the substrate 210 at a plurality of IAB fastener locations 223. The Interface Adapter Board 221 also includes a pair of holes 227 that engage with a pair of IAB alignment pins 224 attached to the substrate 210, which provides for proper alignment of the electrical connector 231. The Interface Adapting Board 221 further includes an orientation phase mark 226 (illustrated in FIGS. 10 and 12), which may be a chamfered corner for example, which provides for proper orientation of the electrical connector 231.

Exemplary embodiments of the CT detector module 200 and 200' provide innovative solutions for mating generic detector packs (such as CdTe or CZT) onto a current platform (for example VCT Lumex™) that shares many components and interfaces. Some embodiments of the invention may include some of the following advantages: (1) the feed through slot 225 allows the use of available module substrate 210 pieces while maintaining short routing to printed circuit board 215; (2) the integrated high voltage elastomer 265 feed through provides simple bias voltage connection to the cathodes 250 that connect automatically when CT detector module 200 is mounted/pressed on to the collimator rails 118; and (3) high precision placement of the high voltage cathode connections.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A computed tomography (CT) detector module, for coupling with a collimator rail, comprising:
    a CT detector pack;
    a printed circuit board;
    an electrical conductor disposed between and in electrical communication with the CT detector pack and the printed circuit board;
    a substrate, having a slot, disposed between the CT detector pack and the circuit board wherein the electrical conductor is routed through the slot; and
    an elastomer conducting contact disposed within the substrate and in electrical communication with the CT detector pack; wherein,
    the elastomer conducting contact is configured to provide a high-voltage anode signal.

2. The CT detector module of claim 1 wherein the substrate is a ceramic or metallic substrate.

3. The CT detector module of claim 1 wherein:
    the substrate further comprises a plurality of mounting pads wherein the mounting pads provide a clearance between the CT detector pack and the collimator rail; and
    the elastomer conducting contact is disposed within at least one of the plurality of mounting pads.

4. The CT detector module of claim 1 wherein the CT detector pack is a cadmium telluride (CdTe) detector pack or a cadmium zinc telluride (CZT) detector pack.

5. The CT detector module of claim 1 wherein the electrical conductor is a flex cable.

6. The CT detector module of claim 1 wherein the electrical conductor is a pin connector.

7. The CT detector module of claim 6 further comprising an Interface Adapting Board electrically connected between CT detector pack and the pin connector.

8. The CT detector module of claim 7 wherein the Interface Adapting Board further comprises a pair of holes wherein the holes engage with a pair of alignment pins attached to the substrate.

9. The CT detector module of claim 7 wherein the Interface Adapting Board further comprises an orientation mark for proper orientation between the Interface Adapting Board and the substrate.

10. A computed tomography (CT) detector array comprising:
    a first collimator rail;
    a second collimator rail, having a high voltage strip, spaced adjacent to the first collimator rail;
    a plurality of CT detector modules, each CT detector module of the plurality of CT detector modules comprising a CT detector pack, a printed circuit board, an electrical conductor disposed between and in electrical communication with the CT detector pack and the printed circuit board, and a substrate, having a slot, disposed between the CT detector pack and the circuit board wherein the electrical conductor is routed through the slot and the substrate is mounted on the first collimator rail and the second collimator rail; and
    an elastomer conducting contact disposed within the substrate and in electrical communication with the CT detector pack; wherein,
    the elastomer conducting contact and the high voltage strip are electrically connected, and
    the elastomer conducting contact and the high voltage strip are configured to provide a high-voltage anode signal.

11. The CT detector array of claim 10 wherein the substrate further comprises a plurality of alignment pins wherein the alignment pins provide for aligned mating between the substrate and the collimator rails.

12. The CT detector array of claim 10 further comprising a plurality of collimator plates disposed between the first collimator rail and the second collimator rail.

13. The CT detector array of claim 10 wherein:
    the substrate further comprises a mounting pad, wherein the mounting pad provides a clearance between the CT detector pack and the collimator plates; and
    the elastomer conducting contact is disposed within the mounting pad.

14. The CT detector array of claim 10 further comprising a threaded block, adjacent to the substrate, wherein the threaded block receives a fastener securing the substrate to the collimator rails.

15. The CT detector array of claim 10 wherein the CT detector pack is a cadmium telluride (CdTe) detector pack or a cadmium zinc telluride (CZT) detector pack.

16. The CT detector array of claim 10 wherein the substrate is a ceramic or metallic substrate.

17. A method for electrically connecting a computed tomography (CT) module to a CT system, the method comprising:
   attaching a CT detector pack to a substrate having a slot;
   routing an electrical conductor through the substrate slot wherein the routing of the electrical conductor is from the CT detector pack to a printed circuit board;
   routing an elastomer conducting contact within mounting pads of the substrate; and
   mounting the substrate to a plurality of collimator rails;
   wherein,
      an electrical connection is formed in response to the mounting of the substrate to the collimator rails; and
      a high-voltage bias connection is formed between the elastomer conducting contact and a high voltage strip of one of the collimator rails in response to the mounting of the substrate to the collimator rails.

18. The method of claim 17 wherein the mounting of the substrate to the collimator rails results in a press fit electrical connection.

19. The method of claim 17 wherein the substrate further comprises alignment pins and the mounting of the substrate to the collimator rails further comprises aligning the substrate to the collimator rails.

\* \* \* \* \*